United States Patent [19]

Jayaweera et al.

[11] Patent Number: 5,425,871
[45] Date of Patent: Jun. 20, 1995

[54] SOLID STATE REFERENCE ELECTRODE FOR HIGH TEMPERATURE ELECTROCHEMICAL MEASUREMENTS

[75] Inventors: Palitha Jayaweera, Fremont; Thomas O. Passell, Palo Alto; Peter J. Millett, Half Moon Bay, all of Calif.

[73] Assignee: Electric Power Research Institute, Palo Alto, Calif.

[21] Appl. No.: 266,426

[22] Filed: Jun. 27, 1994

[51] Int. Cl.6 ............................................. G01N 27/30
[52] U.S. Cl. ..................................... 204/435; 204/400
[58] Field of Search ................................. 204/400, 435

[56] References Cited

U.S. PATENT DOCUMENTS

| | | | |
|---|---|---|---|
| 2,846,386 | 8/1958 | Ingruber | 204/435 |
| 4,003,814 | 1/1977 | Tarassoff et al | 204/422 |
| 4,659,451 | 4/1987 | Fujita et al. | 204/435 |
| 4,888,102 | 12/1989 | Kessie | 204/435 |
| 5,043,053 | 8/1991 | Indig et al. | 204/435 |
| 5,192,414 | 3/1993 | Indig et al. | 204/435 |
| 5,234,570 | 8/1993 | Taylor et al. | 204/435 |
| 5,238,553 | 8/1993 | Hettiarachchi et al. | 204/435 |
| 5,262,038 | 11/1993 | Indig et al. | 204/435 |

OTHER PUBLICATIONS

Agrawal et al, "A Silver—Silver Chloride Reference Electrode for the High Temperature and High Pressure Electrochemistry", *Corrosion—NACE*, vol. 33, No. 11, Nov., 1977, p. 418–419.

*Primary Examiner*—T. Tung
*Attorney, Agent, or Firm*—Flehr, Hohbach, Test, Albritton & Herbert

[57] ABSTRACT

A solid state reference electrode which is stable over a wide range of temperatures, pressures and chemical conditions is provided. The subject reference electrode comprises a zirconia or yttria stabilized zirconia tube having a distal, closed end and a proximal, open end. An opening in the distal end of the tube provides for ionic conduction between the electrolyte inside of the tube and fluid outside of the tube. Inside the tube is an electrolyte containing zirconia, alumina, potassium chloride and silica. Positioned in the electrolyte composition, near the proximal end of the zirconia tube, is a sensing element. A sealing means at the proximal end of the tube seals the inside of the tube and connects the tube to a stainless steel casing. An electrical lead extends from the sensing element through the sealing means. The electrode comprises means for maintaining a constant temperature in the region of the electrolyte composition occupied by the sensing element.

9 Claims, 4 Drawing Sheets

SOLID STATE REFERENCE ELECTRODE FOR HIGH TEMPERATURE ELECTROCHEMICAL MEASUREMENTS

TECHNICAL FIELD

The technical field of this invention is reference electrodes.

BACKGROUND

A variety of electrochemical applications are based on electrochemical cells which contain a reference electrode as one of the electrodes in the cell. The term "reference electrode" is used to refer to an electrode which provides a stable, constant potential regardless of the type, or concentration, of species present in the fluid in which the reference electrode is placed. Thus, one can detect meaningful changes in the potential of an indicator electrode which is paired with a reference electrode. These meaningful changes can be detected by comparing the changes in the paired indicator electrode to the constant potential of the reference electrode. These comparative changes can be used in detecting the presence of a wide variety of species in a solution, where the species influences the potential at the indicator electrode.

Many different reference electrode structures have been designed for use under a variety of conditions, e.g. temperature, pressure and chemical conditions. Exemplary reference electrodes include the hydrogen electrode, the calomel electrode and the silver/silver chloride electrode. Although each of these reference electrodes provides a constant potential in the environments for which they are designed, these electrodes have limitations as to the temperature, pressure and chemical conditions in which they may be employed. For example, hydrogen electrodes cannot be used in oxidizing or reducing environments, or in solutions which poison the metal of the electrode. Saturated calomel electrodes can be used with a wider array of solutions, but are limited to operation at room temperature because of chemical, mechanical and safety concerns.

Thus, there is continuing interest in the development of new reference electrode structures which are stable under a wide range of conditions. Such electrodes would not be limited to a particular use, thus allowing for greater flexibility in application.

RELEVANT LITERATURE

U.S Pat. No. 5,043,053 describes a reference electrode comprising a metal/metal oxide sensing element with a zirconia membrane electrolyte suitable for use at temperatures in excess of 150° C. This electrode structure is suitable for use as a reference electrode where water conditions are constant, e.g. at constant pH.

U.S. Pat. No. 5,192,414 describes a metal cap electrode for evaluating the electrochemical corrosion potential for various metals under high temperature and pressure conditions. The disclosed electrode can be used as a reference electrode where the pH is known and remains constant.

U.S. Pat. No. 5,238,553 discloses a solid state reference electrode comprising an electrolyte of silver chloride dispersed in glass. This electrode is suitable for use as a reference electrode at temperatures above 330° C. Below this temperature, the potential of this reference electrode is unstable because of low ionic conduction of the glass matrix.

SUMMARY OF THE INVENTION

A solid state reference electrode capable of providing a stable, constant potential under a wide range of temperatures and chemical conditions is provided. The subject electrode comprises a zirconia or yttria stabilized zirconia tube having an open proximal end and a closed distal end. At the distal end of the tube is an opening which provides for contact of fluid from the outside to the inside of the tube, thereby providing a continuous ionic conductive pathway between the electrolyte inside of the tube and the fluid outside of the tube. Inside the tube is an electrolyte containing zirconia, alumina, potassium chloride and silica. Positioned in the electrolyte near the proximal end of the tube is a sensing element. The proximal end of the tube is sealed with a sealing means. Extending from the sensing element through the sealing means is an electrical lead. The tube is housed in a stainless steel casing supporting the tube at the proximal end. The electrode includes a means for maintaining an optimum temperature in the region of the electrolyte which is occupied by the sensing element.

DESCRIPTION OF THE SPECIFIC EMBODIMENTS

Figure 1:
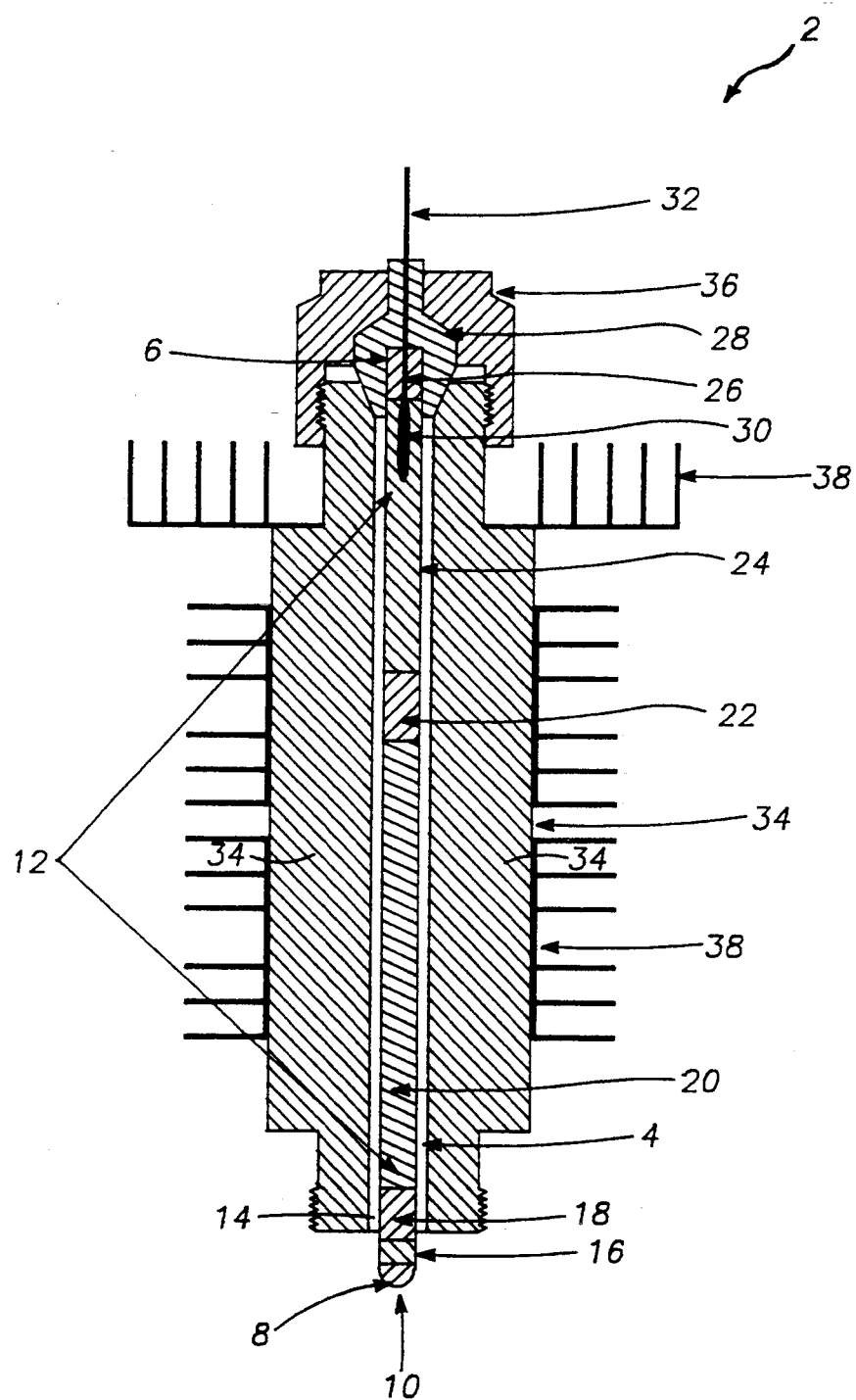
FIG. 1 is a cross-sectional view of a solid state reference electrode in accordance with the invention.

A solid state reference electrode which provides a stable, constant potential over a wide range of chemical and temperature conditions is provided. The electrode comprises a zirconia tube having a closed, distal end and an open, proximal end. The closed, distal end has an opening which provides contact of fluid from the outside to the inside of the tube, thereby providing for a continuous ionic conductive pathway between the electrolyte inside of the tube and the fluid outside of the tube. Inside the tube is an electrolyte containing zirconia, alumina, potassium chloride and silica. In the electrolyte, near the proximal end of the tube, is a sensing element. The proximal end of the tube is sealed with a sealing means. Extending from the sensing element through the sealing means is an electrical lead. The tube is supported from the distal end in a stainless steel casing. A temperature control means maintains an optimum temperature in the region of the electrolyte composition occupied by the sensing element.

In the subject reference electrode, an electrolyte composition is contained within a hollow, closed end tube. The tube may be made of any suitable material which is inert to high temperature, pressure and varying chemical environments. Exemplary materials include zirconia and yttria stabilized zirconia. The tube is open at a proximal end and closed at a distal end. The distal end has a small opening which provides for contact between electrolyte inside the tube and the fluid outside the tube, providing for a continuous ionic conductive pathway between the electrolyte inside of the tube and fluid outside of the tube.

The tube serves to house an electrolyte. As used here, the term electrolyte is not limited to the traditional physical chemistry definition of electrolyte, i.e. a substance which, when dissolved in a specified solvent, usually water, produces an ionically conducting solution. Instead, the term electrolyte is used in the broader sense to refer to any conducting medium in which the flow of electric current takes place by migration of ions. In the subject invention, the electrolyte present in the tube will contain zirconia, alumina, potassium chloride and silica gel. A small amount of water is adsorbed onto the silica gel and alumina in the electrolyte. The potassium chloride dissolves in this adsorbed water to provide migrating chloride ions in the electrolyte.

The various components or compounds which make up the electrolyte are arranged in layers from the distal to proximal end of the tube. The preferred first layer of the tube is made of zirconia ($ZrO_2$). The pure zirconia layer will make up roughly 12.5% of the electrolyte composition. The zirconia layer contains a coarse particle and a fine particle layer of zirconia. The coarse particle layer is the layer closest to the distal end of the tube. The coarse particle layer will usually make up about 33% of the total zirconia layer. The coarse particles will range in size from 100 to 1000 $\mu$m, usually 200 to 250 $\mu$m. The fine particle layer on top of the coarse particle layer will usually make up about 66% of the total zirconia layer. The average particle size in the fine zirconia layer will range from about 0.3 to 5.0 $\mu$m, more usually from about 0.3 to 1.0 $\mu$m.

Layered on top of the zirconia layer will be a first composite layer containing zirconia, alumina ($Al_2O_3$) and potassium chloride (KCl). In this composite layer, the zirconia will make up roughly 85 to 90% of the total composite, more usually about 87% of the total composite. The particle size of the zirconia in this layer will range from about 0.2 to 5.0 $\mu$m. The alumina present in this composite layer will make up roughly 8 to 12% of the total composite layer, usually about 10% of the total composite layer. The particle size of the alumina will range from about 0.2 to 5.0 $\mu$m, more usually from about 0.2 to 1.0 $\mu$m. Potassium chloride will make up the remainder of the composite, usually being about 2 to 5% of the total composite, more usually about 3% of the total first composite layer. The various components in this, as well as the following composite layers, will be evenly dispersed throughout the layer. Generally, the first composite layer will make up about 40 to 50% of the total of the electrolyte composition.

Layered on top of this first composite layer will be a second composite layer made up of potassium chloride and alumina. In this second composite layer, the potassium chloride will be 85 to 95% of the total composite, usually about 90% of the total composite of the second layer. The alumina will make up about 5 to 15% of the total composite, usually about 10% of the total composite. The second composite layer will make up less that 5% of the total electrolyte composition.

The next layer in the electrolyte composition will be a third composite layer made up of potassium chloride and silica. The silica, or silica gel, will make up about 45 to 55% of this third composite layer, more usually about 50% of the third composite layer. The remainder of the third composite layer will be potassium chloride. This third composite layer will make up about 33% of the total electrolyte composition.

The final layer of the electrolyte composition will be a layer of essentially pure potassium chloride. This potassium chloride layer will make up about 3 to 5% of the total electrolyte composition, and will more usually be about 4% of the total composition.

Positioned in the electrolyte composition is a sensing element. Typically, the sensing element will be a metal/metal chloride sensing element, particularly silver/silver chloride (Ag/AgCl). The sensing element will be positioned in the third composite layer of the electrolyte composition, i.e. the silica/potassium chloride layer. Specifically, the sensing element will be placed in the region of the third composite layer that is nearest the proximal end of the tube.

At the proximal end of the tube will be a sealing means which serves to seal the inside of the tube. In sealing the inside of the tube, the sealing means serves to: (1) provide a pressure boundary between the outside and inside of the zirconia tube and the ambient exterior pressure, and (2) provide for electrical isolation between the stainless steel electrode housing and the sensor element lead. The sealing means also serves as a connection between the tube and the stainless steel casing in which the tube is positioned.

Any convenient sealing means may be employed, where the material used for the sealant is inert to changes in temperature and pressure, as well as changes in the chemical environment of the electrode. Suitable materials include high temperature TEFLON ® (polytetrafluoroethylene), which may include heat resistant fillers, such as fiber glass, quartz, ceramic fibers or mica. One exemplary type of sealing material is RULON ® (polytetrafluoroethylene + heat resistant filler).

Extending from the sensor element through the sealing means is an electrical lead for connecting the sensing element to a means for monitoring the potential of the reference electrode. Any convenient electrical lead material may be used to connect the sensing element to a means for monitoring the potential of the reference electrode. Usually, where the sensing element is Ag/AgCl, the lead material will be silver.

The stainless steel casing is a hollow cylinder having a top and bottom ends. The top end of the cylinder will be connected to the tube by the sealing means. The relationship between the tube and the stainless steel casing may be secured by a fastening means, such as a stainless steel nut or the like. The inner diameter of the cylinder will be of sufficient width to surround the tube with an annular space. The distal end of the tube will extend a short distance below the bottom of the stainless steel cylinder.

The subject electrode will usually contain a means for maintaining an optimal temperature in the electrolyte composition in the region of the sensing element. Optimal temperatures for the electrolyte composition in the sensing element region will be from about 20° to 80° C., and will usually be about 25° C. Any convenient temperature control means may be employed. Suitable means include heat sinks fitted onto the stainless steel outer casing, forced air, water cooling and the like.

One embodiment of the solid state reference electrode will be further described with reference to FIG. 1 which is a cross sectional view of a solid state reference electrode 2. In the present example, the electrode has a length of 6.0 in. Zirconia tube 4 has an open, proximal end 6 and a closed, distal end 8. The closed distal end 8 has an opening 10 which is between 0.020 and 0.040 inches in diameter. Inside the zirconia tube is an electrolyte composition 12. The electrolyte 12 is made up of several distinct layers. The first layer of the electrolyte composition, in ascending order from the distal end of the tube, is a pure zirconia layer 14. The zirconia layer 14 is 0.75 in. in length and is made of coarse particle zirconia layer 16 and a fine particle zirconia layer 18. The coarse particle zirconia layer 16 is 0.25 in. long and is positioned next to the opening 10. The fine particle zirconia layer 18 is 0.5 in. long. Layered on top of the zirconia layer 14 is the first composite layer 20. The first composite layer 20 comprises a mixture of 87% zirconia, 10% alumina and 3% potassium chloride. The first composite layer is 2.75 in. long. Layered on top of the first composite layer is a second composite layer 22. The 0.25 in. long second composite layer 22 is 90% potassium chloride and 10% alumina. Layered on top of the second composite layer is a third composite layer 24 which is made up of 50% silica and 50% potassium chloride and is 2.0 in. long. Layered on top of the third composite layer is a pure potassium chloride layer 26 which is 0.25 in. long. At the proximal end of the tube is a Rulon ® fitting 28, which seals the tube at the proximal end. The Rulon ® fitting was custom designed from a block of Rulon ®. In the third composite layer, 1.25 in. from the proximal end of the tube, is a silver/silver chloride sensing element 30. Extending from the silver/silver chloride sensing element 30 is silver wire 32 which has a 0.040 in. diameter. Encasing the tube and connected to the tube by the Rulon ® fitting, is a stainless steel casing 34. The relationship between the stainless steel casing and the tube is secured by a stainless steel nut 36 and the Rulon ® fitting. On the outer surface of the stainless steel casing are heat sinks 38 for maintaining an optimum temperature in the region of the electrolyte composition containing the sensing element.

The following examples are provided by way of illustration and not by way of limitation.

EXPERIMENTAL

Example 1

Preparation of a Solid State Reference Electrode

A 6.0 in. long closed-end zirconia tube was drilled at the closed end to make a small opening (0.020–0.040 in. in diameter). The tube was packed with the following layers: 1) $ZrO_2$, 2) $ZrO_2:Al_2O_3:KCl$, 3) $KCl:Al_2O_3$, 4) Silica:KCl and 5) KCl in accordance with the following table.

TABLE

| Layer | Depth (inches) | Composition (%) |
|---|---|---|
| $ZrO_2$ | .75 | 100 |
| a) Coarse $ZrO_2$ | .25 | |
| b) Fine $ZrO_2$ | .50 | |
| $ZrO_2:Al_2O_3:KCl$ | 2.75 | 87:10:3 |
| $KCl:Al_2O_3$ | .25 | 90:10 |
| Silica:KCl | 2.0 | 50:50 |
| KCl | .25 | 100 |

The above layers were tightly packed in the tube. The packed layers were then pressed with an isocratic press at 50,000 psi to further pack the electrolyte composition. A small amount of water was forced into the electrolyte through the small opening in the zirconia tube, where the water adsorbed onto the silica and alumina. Slight variations from the above parameters were found to have no effect on the performance of the electrode.

The silver/silver chloride sensing element was inserted 1.25 inches into the electrolyte composition so that it was positioned in the silica/potassium chloride layer of the electrolyte composition. The proximal end of the zirconia tube was fitted into a Rulon ® fitting, which in turn was fitted into a stainless steel nut. The stainless steel nut was tightened, compressing the Rulon ® fitting to hold the zirconia tube, stainless steel outer casing and stainless steel nut in a leak proof seal. The resultant electrode was then conditioned in distilled water under 1500 psi for 3 hours at room temperature.

The electrochemical equilibrium of the silver/silver chloride sensing element was determined as follows:

$AgCl + Cl^- \rightarrow Ag + Cl^-$ $E_{AgCl/Ag} = E^0_{AgCl/Ag} - (RT/nF)\ln[a_{Cl^-}]$ $E^0_{AgCl/Ag}$ = Standard electrode potential $[a_{Cl^-}]$ = Activity of chloride in saturated KCl solution at the temperature of the reference element zone $E_{AgCl/Ag} = 0.197$ V at 25° C.

Example 2

Performance of the Solid State Reference Electrode

Figure 2:
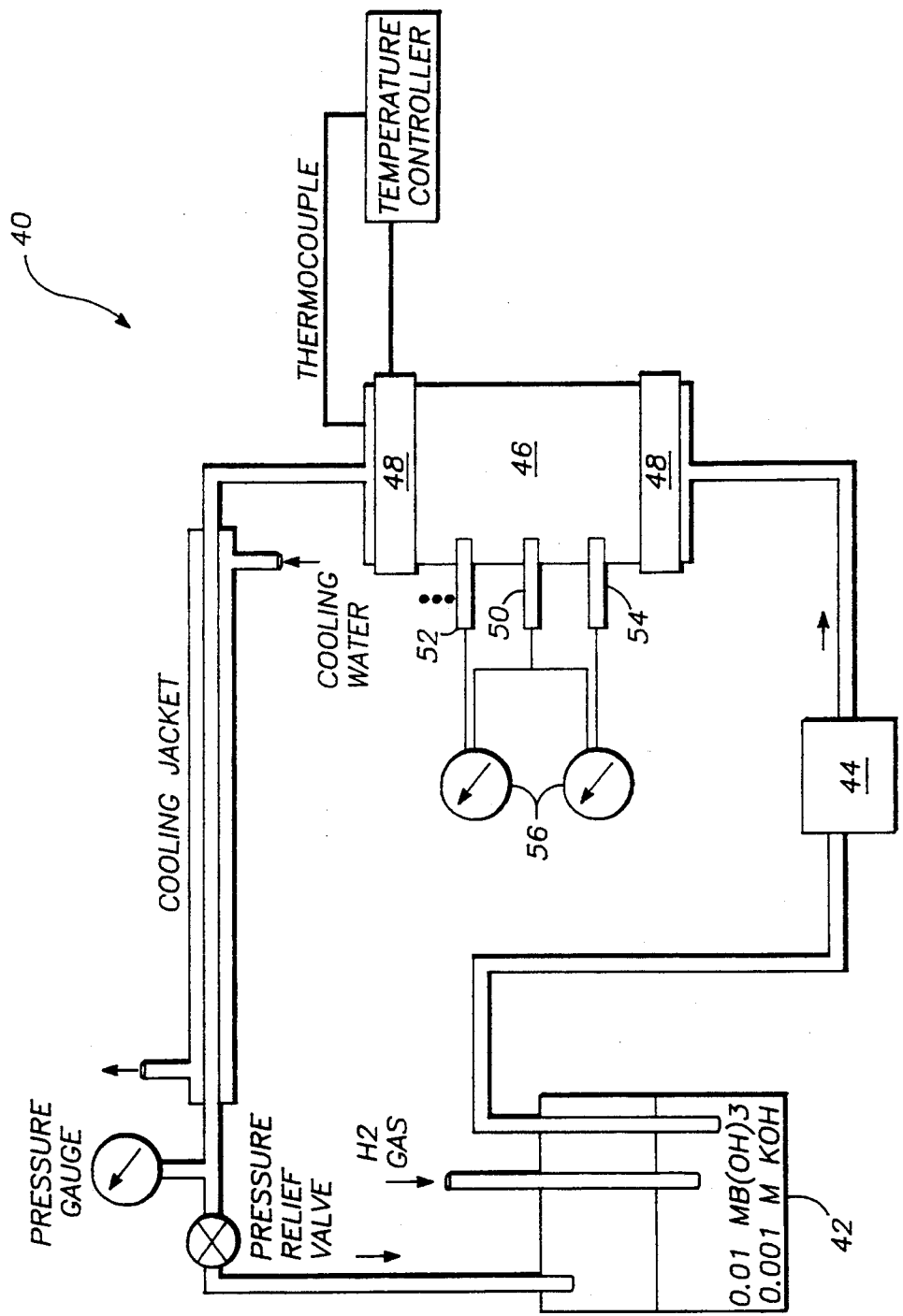
FIG. 2 is a diagram of the recirculating flow loop used for testing the subject electrodes.

The solid state reference electrode was tested in comparison with two standard reference electrodes in a circulating flow loop containing a solution of 0.01M $B(OH)_3 + 0.001M$ KOH. The circulating flow loop is diagrammed in FIG. 2. Circulating flow loop 40 begins at reservoir 42. Fluid is pumped from reservoir 42 by high pressure pump 44 to autoclave 46. The temperature of the fluid in the autoclave was maintained at 280° C. using band heaters 48. Inserted into the autoclave were the subject solid state reference electrode 50, an EPBRE electrode 52 and a hydrogen electrode 54. Volt meters 56 are used to monitor the potential of the electrodes. Fluid returns from the autoclave to the reservoir to complete the loop.

A. The Potential of the Solid State Reference Electrode v. the Potential of an External Pressure Balanced Reference Electrode (EPBRE)

Figure 3:
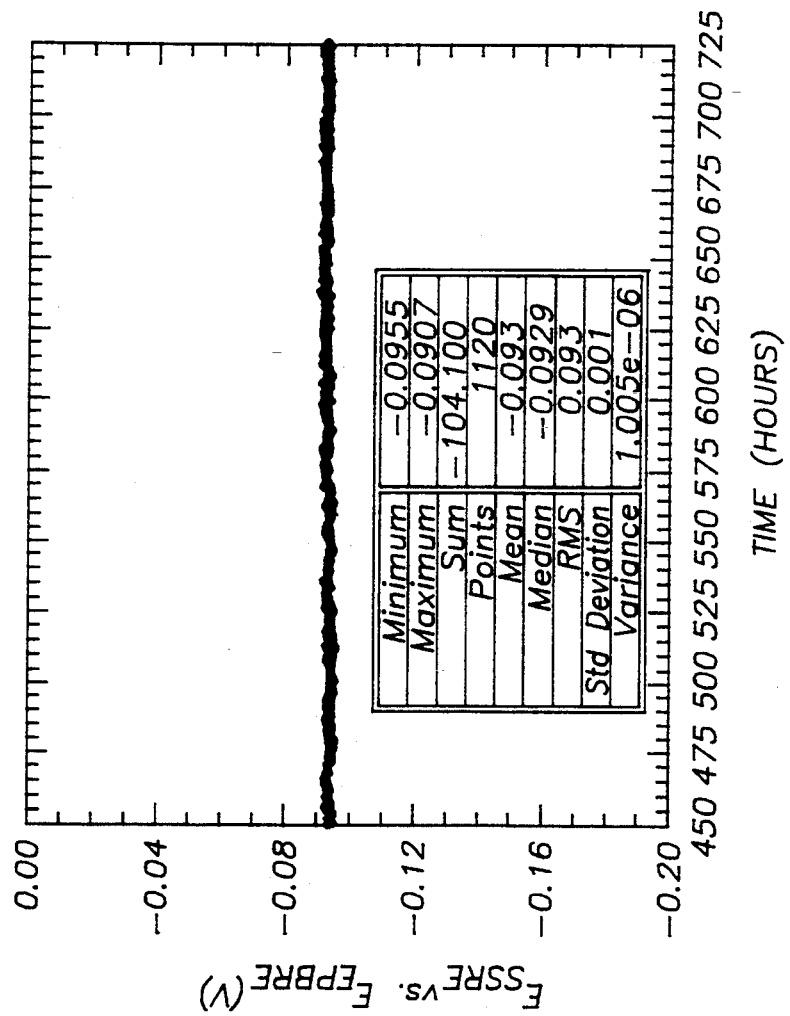
FIG. 3 is a graphical representation of the variation of the potential of the subject electrode as compared with the potential of a external pressure balanced reference electrode in a saturated hydrogen solution.
Figure 4:
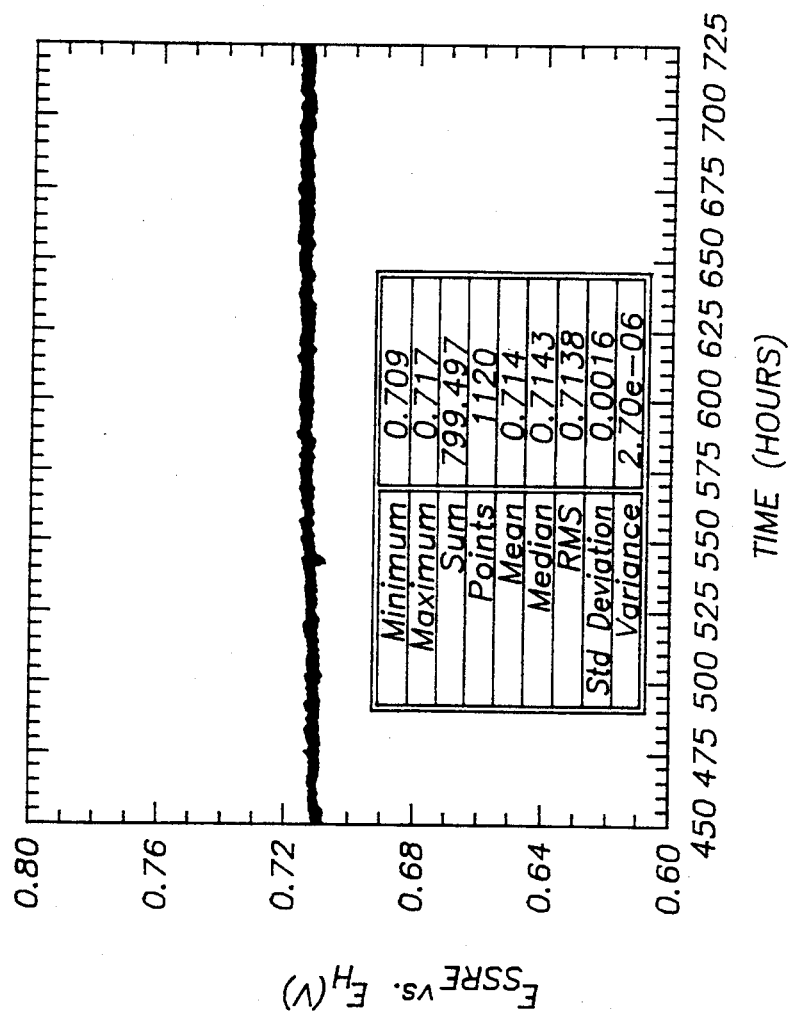
FIG. 4 is a graphical representation of the variation of the potential of the subject electrode as compared with the potential of a hydrogen electrode in a saturated hydrogen solution.

To study the potential provided by the solid state reference electrode under the above conditions, the potential of the reference electrode was monitored and compared with the potential of an EPBRE over a test period of 725 hours. FIG. 3 provides a graphical representation of the results over a 275 hour period from hour 450 to hour 725 of the overall test period. During this time, the electrode potential showed very little variation, with a 1 mV standard deviation. During the test period, the maximum electrode potential was found to be −0.096 V and the minimum electrode potential was found to −0.091 V. The EPBRE was found to have a 6–9 mV drift when measured against a standard calomel electrode. The potentials shown in FIG. 2 have been corrected to account for this drift. The potential of the solid state reference electrode did not drift during the 275 hour period.

From the results shown in FIG. 3, it was concluded that the solid state reference electrode was able to provide a constant, stable potential at high temperatures and in reducing environments.

B. The Potential of the Solid State Reference Electrode v. the Potential of a Hydrogen Electrode Under the same conditions as above, the potential of the solid state reference was measured in relation to a standard hydrogen electrode for a test period of 725 hours. FIG. 3 provides a graphical representation of the potential of the solid state reference electrode as compared to the potential of the standard hydrogen electrode over a 275 hour period of the total test period (hour 450 to hour 725). The electrode potential of the solid state reference electrode was found to be stable during this period, with a standard deviation of only 1.6 mV.

Again, it was concluded that the subject solid state reference electrode was able to provide a stable, constant potential at high temperatures and in a reducing environment.

It is evident from the above experiments and discussion that a reference electrode capable of supplying a stable, constant potential when exposed to a wide range of environments is provided. The reference electrode provides a stable potential at temperatures ranging from 0° C. to supercritical temperatures. The electrode provides a stable potential under various chemical conditions, including reducing conditions. In addition, the electrode does not suffer from long term drift. Thus, the electrode is suitable for use as a reference for electrochemical potentials and pH measurements over a wide range of conditions. Further, the subject solid state reference electrodes will find use in applications, e.g. nuclear and fossil power plants, where operational temperatures, pressure and chemical conditions preclude the use of standard reference electrodes.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A solid state reference electrode comprising:
   (a) a tube inert to high temperature, heat and chemicals having an open proximal end and a closed distal end, wherein said distal end comprises an opening for ionic conduction between the inside and the outside of said tube;
   (b) an electrolyte inside of said tube comprising zirconia, alumina, silica and potassium chloride;
   (c) a sensing element in said electrolyte near the proximal end of said tube;
   (d) a sealing means for sealing said tube at said proximal end; and
   (e) an electrical lead extending from said sensor element through said sealing means and electronically connected to the sensor element.

2. The reference electrode of claim 1, wherein said electrode is housed in a stainless steel casing, wherein said distal end of said tube extends below the bottom of said casing and said casing supports said tube at the sealing means end.

3. The electrode of claim 2, wherein said reference electrode further comprises a means for maintaining an optimum temperature in the region of said electrolyte occupied by said sensing element.

4. The electrode of claim 3, wherein said means for maintaining an optimum temperature is a heat sink on the outer surface of said stainless steel casing.

5. A solid state reference electrode comprising:
   (a) a tube inert to high temperature, heat and chemicals having an open proximal end and a closed distal end, wherein said distal end comprises a small opening for ionic conduction between the outside and inside of said tube;
   (b) an electrolyte inside of said tube, said electrolyte comprising, in the direction from said distal end:
   a layer of coarse zirconia;
   a layer of fine zirconia;
   a layer comprising zirconia, alumina and potassium chloride;
   a layer comprising alumina and potassium chloride;
   a layer comprising silica and potassium chloride; and
   a layer of potassium chloride;
   (c) a silver chloride sensing element near the proximal end of said tube in said layer of silica and potassium chloride;
   (d) a sealing means for sealing said proximal end; and
   (e) a silver lead extending from said sensor element through said sealing means.

6. The reference electrode of claim 5, wherein said opening has a diameter between 0.02 and 0.04 in.

7. The reference electrode of claim 5, wherein said tube is housed in a stainless steel casing, wherein said distal end of said tube extends below an end of said casing and said casing supports said tube at the sealing means end.

8. The electrode of claim 7, further comprising a heat sink on said casing.

9. The electrode of claim 5, wherein said tube is made of one of zirconia and yttria stabilized zirconia.

* * * * *